US006645166B2

United States Patent
Scheunert et al.

(10) Patent No.: US 6,645,166 B2
(45) Date of Patent: Nov. 11, 2003

(54) BLOOD TREATMENT DEVICE AND DISPOSABLE KIT FOR A BLOOD TREATMENT DEVICE

(75) Inventors: Peter Scheunert, Friedrichsdorf (DE); Martin Lauer, St. Wendel (DE); Manfred Weis, St. Wendel (DE); Josef Beden, Mainz-Kastel (DE); Martin Herklotz, Heusenstamm (DE); Joachim Manke, Löhnberg (DE); Uwe Hahmann, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/940,389

(22) Filed: Aug. 27, 2001

(65) Prior Publication Data

US 2002/0041825 A1 Apr. 11, 2002

(30) Foreign Application Priority Data

Aug. 29, 2000 (DE) .......................... 100 42 324

(51) Int. Cl.[7] .......................... A61M 37/00; A61M 3/00; C02F 1/44
(52) U.S. Cl. .......................... 604/6.11; 604/43; 210/645
(58) Field of Search .................. 422/44–48; 604/6.05, 604/6.06, 6.09, 6.11, 6.1, 43; 210/645, 646, 85

(56) References Cited

U.S. PATENT DOCUMENTS 4,486,189 A    12/1984  Troutner et al.

FOREIGN PATENT DOCUMENTS

| DE | 33 28 744 | 2/1985 |
| DE | 39 11 587 | 9/1998 |
| DE | 198 14 695 | 10/1999 |
| WO | 84/02473 | 7/1984 |
| WO | 98/22165 | 5/1998 |
| WO | 99/17019 | 4/1999 |

*Primary Examiner*—Angela D. Sykes
*Assistant Examiner*—Leslie R Deak
(74) *Attorney, Agent, or Firm*—Kenyon & Kenyon

(57) ABSTRACT

A blood treatment device, in particular a dialysis machine, which permits both single-needle and dual-needle operation. The device has a blood treatment unit, in particular a dialyzer that has an inlet connected to a feed line and an outlet connected to a return line. The feed line has two parallel line branches with a positive displacement pump being connected into the first and second line branches. To produce a fluid connection between the outlet of the dialyzer and one of the two pumps, a connection line is provided. For dual-needle operation, the feed and return lines are connected to an arterial and a venous needle. For single-needle operation, the feed and return lines are brought together and connected to a common needle. The connection line permits single-needle operation without great changes to the structure of the blood treatment device.

16 Claims, 3 Drawing Sheets

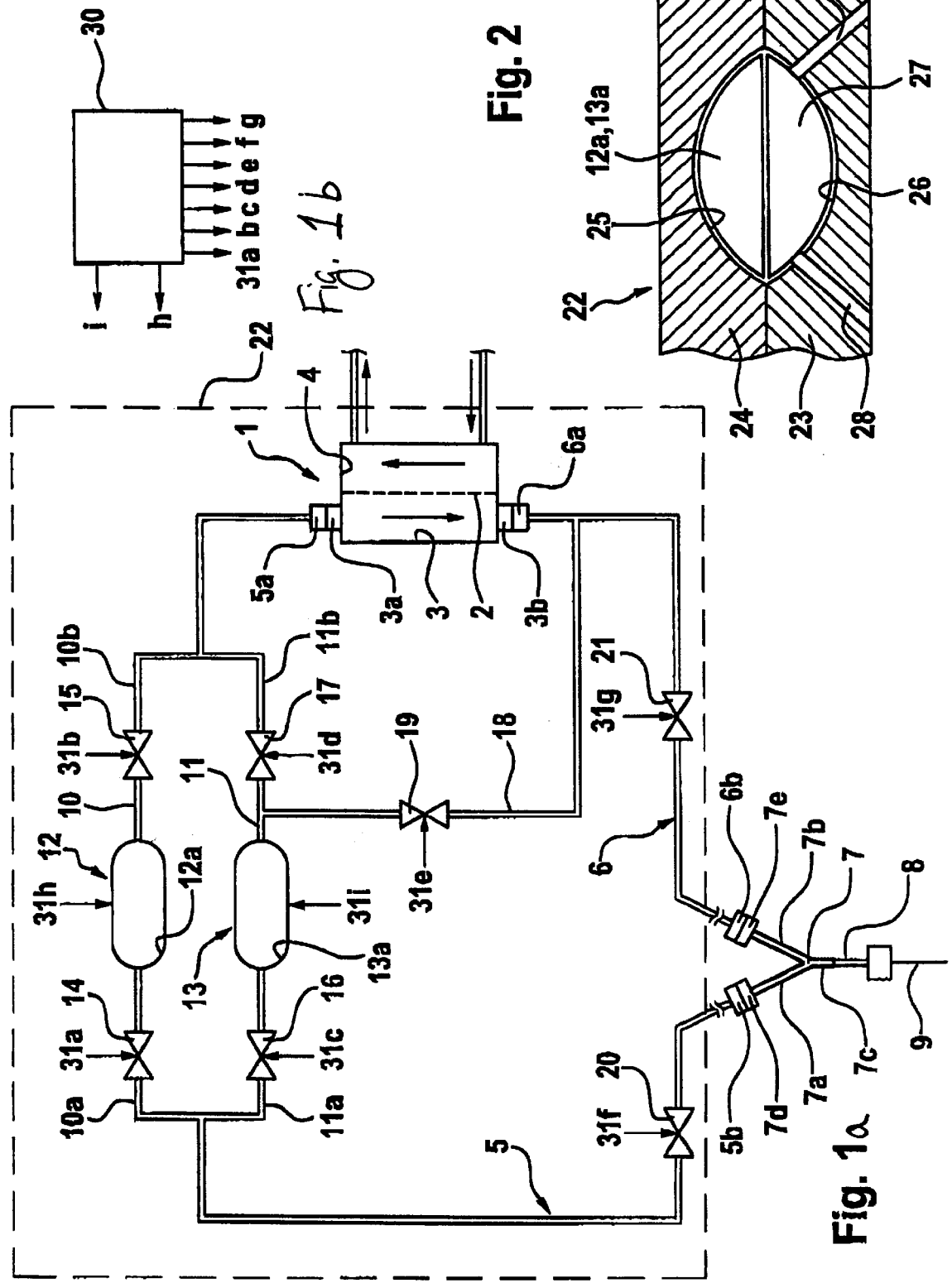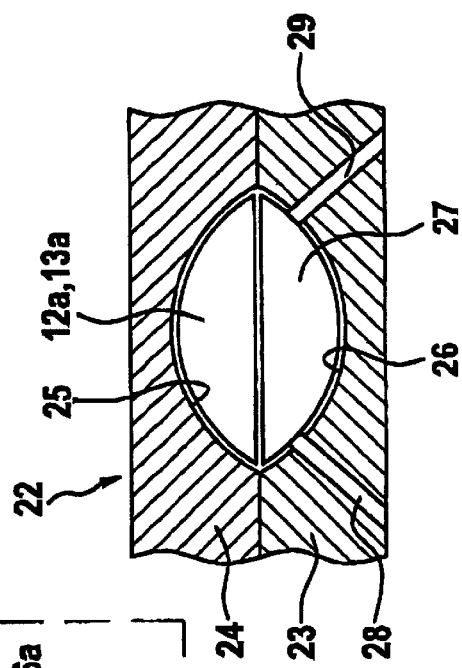

BLOOD TREATMENT DEVICE AND DISPOSABLE KIT FOR A BLOOD TREATMENT DEVICE

FIELD OF THE INVENTION

The invention relates to a blood treatment device, in particular a dialysis machine, which has a blood treatment unit, in particular a dialyzer. The invention further relates to a disposable kit for such a blood treatment device.

BACKGROUND OF THE INVENTION

Various dialysis methods are known. In dual-needle dialysis, blood is drawn off from a patient via one needle and returned to the patient via another needle. In this case, the blood is pumped continuously through the dialyzer. Single-needle dialysis requires only one needle in order to draw off and return blood cyclically, as the arterial and venous blood lines are connected to the same needle.

Single-needle and dual-needle dialysis machines generally make use of occluding tube pumps. Dialysis machines are known, however, in which positive displacement pumps are used to pump the blood.

DE 39 11 587 A1 describes a single-needle dialysis machine, in which the blood, in a first phase, is drawn off by a needle via an arterial branch and, in a second phase, is returned via a venous branch by the same needle. In order to make it possible to achieve continuous blood flow via the dialyzer, even in the case of single-needle dialysis, compensation chambers are connected into the arterial and venous branches. Single-needle dialysis is less stressful for the patient, but the control of the blood flow via the common needle is more demanding than in the case of dual-needle dialysis.

WO84/02473 and WO98/22165 disclose blood treatment devices in which various components that form a functional unit are combined in a cassette. This modular design has the advantage that the parts of the system coming into contact with the blood can be replaced easily. A disadvantage, however, is that the flow plan is dictated by the design of the model. If, for example, the module is to be configured for dual-needle operation, then single-needle operation is not possible, or vice versa.

SUMMARY OF THE INVENTION

It is an object of the invention to offer a blood treatment device which allows both single-needle and dual-needle operation, without great changes having to be made to the flow plan of the device. It is another object of the invention to provide a disposable kit for such a blood treatment device.

These objects are achieved according to the invention by providing, for example, a blood treatment device that includes a blood treatment unit having an inlet and an outlet. A feed line is connected to the inlet of the blood treatment unit, the feed line has a first branch line and a second branch line. Also provided is a return line connected to the outlet of the blood treatment unit. Included is a first positive displacement pump connected in the first line branch, the first pump divides the line branch into a first section and a second section. A first closure member is provided in the first section of the first line branch, and a second closure member is provided in the second section of the first line branch. Additionally, a second positive displacement pump is connected in the second line branch, the second pump divides the second line branch into a first section and a second section. A third closure member is provided in the first section of the second line branch, a fourth closure provided in the second section of the second line branch. A connection line, having a fifth closure member, connects the outlet of the blood treatment unit to the first line branch or the second line branch.

The term blood treatment device is intended to mean all devices that have an extracorporeal circuit with a unit for treating blood. These include, in particular, devices for hemodialysis, hemofiltration and hemodiafiltration but also, for example, cell separators.

For the delivery of blood, the blood treatment device has two positive displacement pumps, preferably diaphragm pumps, with the first pump being connected into the first line branch and the second pump being connected into the second line branch of a branching feed line, through which the blood is drawn off from the patient and supplied to the blood treatment unit, for example the dialyzer. The blood from the blood treatment unit is returned via a discharge line.

For dual-needle operation, a needle is attached both to the feed line and the return line. The two pumps operate alternatively. While one pump is taking blood in, the other pump delivers blood into the blood treatment unit, so that blood flows continuously through the blood treatment unit.

A connection line for producing a fluid connection between the outlet of the blood treatment unit and one of the two pumps permits single-needle operation without great changes to the flow plan. The feed and return lines are connected to a common needle during single-needle operation. In a first phase, both pumps take blood in via the open fluid connection, with the blood flowing through the first pump and the blood treatment unit to the second pump. The blood is not returned via the return line in this phase. In a subsequent second phase, the fluid connection remains open, with both pumps delivering blood that is returned via the return line.

In an alternative embodiment, the common needle may be attached only to the feed line, with the blood being drawn off and returned only via the feed line in this embodiment.

The parts of the blood treatment device that come into contact with the blood are preferably designed as a disposable kit, although they may also be part of the blood treatment device.

The disposable kit for the blood treatment device has a feed line with two parallel line branches, and a return line, and pump chambers connected into the first and second line branches, as well as a connection line. The disposable kit may, however, also comprise yet other components, for example main chambers etc. The blood treatment unit may also be part of the disposable kit.

The disposable kit may be designed as a tube set. It is, however, also possible to fit all parts of the disposable kit in one functional unit, for example in the form of a film part.

The blood treatment unit preferably has a holding unit, known from the prior art, into which the disposable kit is put. The pumps and closure members for controlling the blood flow are then part both of the disposable kit and of the holding unit. Disposable kits and holding units having such pumps and closure members are, for example, described in DE 198 14 695 A1, and WO 99/17019, the disclosure of which is herein incorporated by reference.

The advantages of the invention are most pronounced when the parts coming into contact with the blood are designed as a disposable kit, which is put into the holding unit on the machine side. To perform single-needle operation, only minor changes need to be made to the disposable kit and to the holding unit. To that end, only a short sealable tap line is required, which should be as short as possible so that the dead volume is small.

BRIEF DESCRIPTION OF THE DRAWINGS

Several exemplary embodiments of the invention will be explained in more detail below with reference to the drawings, in which:

FIG. 1a shows the essential components of a blood treatment device for single-needle operation in a simplified representation;

FIG. 1b shows a schematic illustrating the operation of a control unit connected to the blood treatment device shown in FIGS. 1a, 3, and 4;

FIG. 2 shows a simplified representation of the part that holds a pump chamber of the disposable kit, in the holding unit of the blood treatment device of FIG. 1a;

DETAILED DESCRIPTION OF THE DRAWINGS

Figure 3:
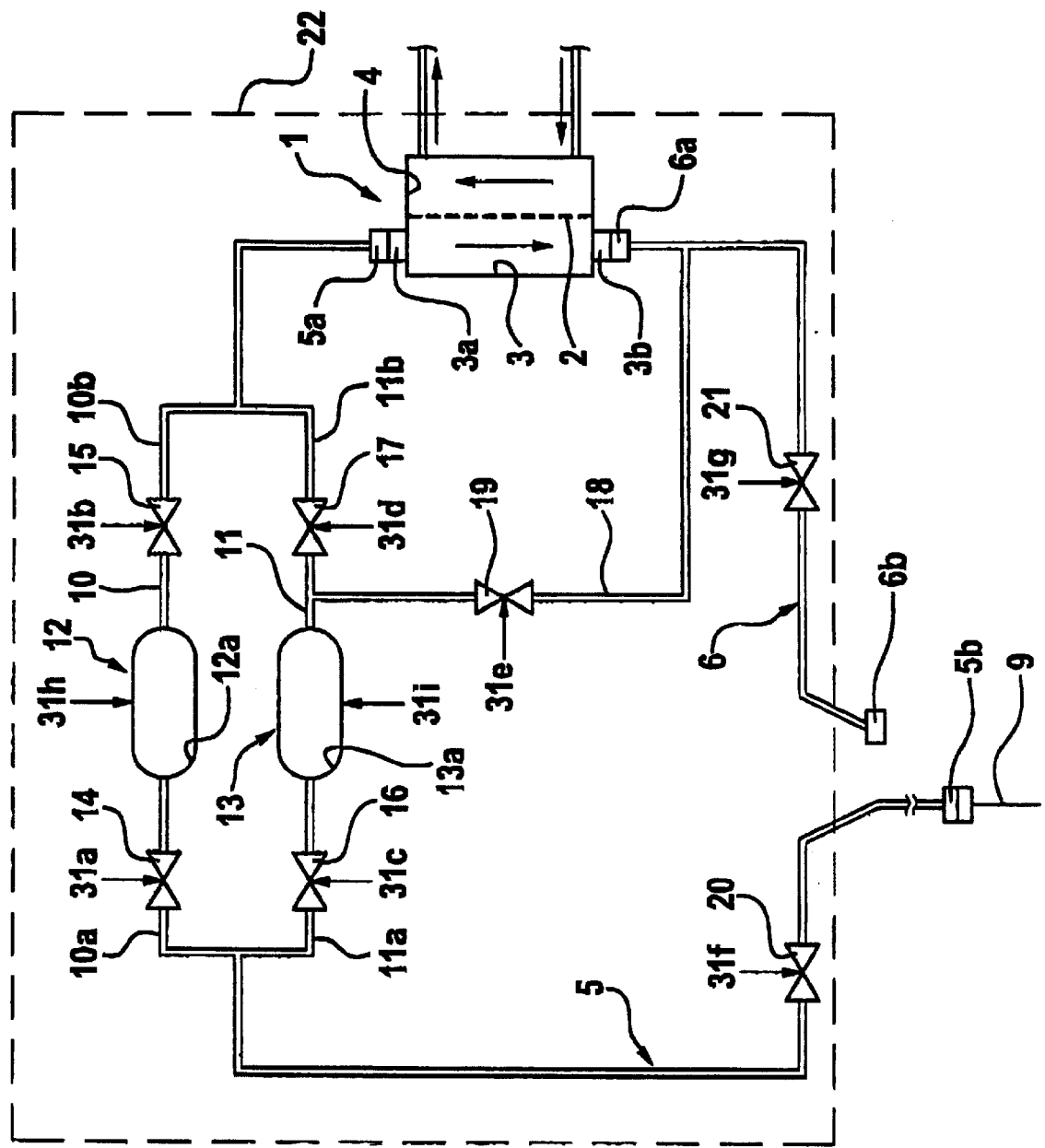
FIG. 3 shows an alternative embodiment of the blood treatment device for single-needle operation.

FIG. 1a shows the essential components of the blood treatment device that has a blood treatment unit 1. Blood treatment unit 1 may, for example, be a dialyzer that is divided by a semipermeable membrane 2 into a blood chamber 3 and a dialyzer fluid chamber 4. During the dialysis treatment, blood flows through blood chamber 3 and dialyzer fluid flows through the dialyzer fluid chamber 4. The flow directions are marked by arrows in FIG. 1a.

A patient's blood is supplied to the blood chamber 3 of the dialyzer 1 via a feed line 5, and is returned from the blood chamber via a return line 6. The feed and return lines 5, 6 respectively have connectors 5a, 5b and 6a, 6b at their ends. The feed and return lines are attached to the inlet and outlet 3a, 3b of the blood chamber by means of the connectors 5a, 6a.

For single-needle dialysis, the free ends of the feed and return lines 5, 6 are connected by means of a Y-connection piece 7 that has two individual line branches 7a, 7b and a common line branch 7c. To attach the Y-connection piece 7, the connectors 5b, 6b of the feed and return lines 5, 6 are connected respectively to the corresponding connectors 7d, 7e of the connection piece. A common blood line 8, to which a common needle 9 is attached, is connected to the common line branch of the connection piece 7.

The feed line 5 has two parallel line branches 10, 11, with one positive displacement pump, preferably a diaphragm pump 12, being connected into the first line branch 10 and a second positive displacement pump, preferably a diaphragm pump 13, being connected into the second line branch 11. A first closure member 14 is arranged in the line section 10a of the first line branch 10 leading to the first pump 12, a second closure member 15 is arranged in the line section 10b of the first line branch 10 leading off from the first pump, a third closure member 16 is arranged in the section 11a of the second line branch 11 leading to the second pump 13 and a fourth closure member 17 is arranged in the line section 11b of the second line branch 11 leading off from the second pump.

To produce a fluid connection between the outlet of the blood chamber 3 and the second pump 13, a connection line 18 is provided that branches off from the return line 6 and is attached to the second line section 11b of the second line branch 11 between the second pump 13 and the fourth closure member 17. A fifth closure member 19 is provided in the connection line 18. A sixth closure member 20 is provided at the feed line 5, and a seventh closure member (additional closure member) 21 is provided at the return line 6. The sixth closure member in the feed line is not, however, compulsory in this embodiment.

The feed and return lines 5, 6 and the connection line 18 are designed, together with the pump chambers 12a, 13a of the pumps 12, 13, as a disposable kit that is put into a holding unit 22 (represented only by way of indication by broken lines) of the blood treatment device.

FIG. 2 shows the part in the holding unit 22 that holds the pump chamber of the pump 12. However, it is understood that holding unit 22 may also hold the pump chamber 13a of the pump 13. The holding unit 22 consists of a lower and an upper housing body 23, 24, respectively, each of which has a trough-like recess 25, 26. The lower trough-like recess 25 holds a pressure chamber 27 which is alternately filled with and emptied of a gas or a liquid via inlet and outlet channels 28, 29, respectively. The pump chamber 12a or 13a of the first or second pump 12, 13, is put into the upper trough-like recess 26. During filling, the pressure chamber 27 inflates so that the pump chamber 12a or 13a is compressed (the delivery operation). When the pressure chamber is being emptied, the pump chamber expands (the intake operation). Such holding units are known, for example, from WO 99/17019, which is fully incorporated herein.

As shown in FIG. 1b, the closure members are clamp devices that engage on the lines, and are electromagnetically or pneumatically actuated by a control unit 30 that is connected via control lines 31a to 31g to the respective individual closure members shown in FIG. 1. The control unit 30 is further connected via control lines 31h, 31i to the two pumps 12, 13.

For single-needle dialysis, the disposable kit is put into the holding unit 22, and the dialyzer 1 and the Y-connection piece 7 are attached. The control unit 30 drives the pumps 12, 13 and the closure members set forth below.

Initially, all the closure members are closed. At the start of a first phase, the control unit 30 opens the first, second, fifth and sixth closure members 14, 15, 19, 20, and switches the first and second pumps 12, 13 to intake operation. The first and second pumps 12, 13 now take in blood from the patient through the needle 9 until both pump chambers 12a, 13a are filled with a particular fluid volume. In this case, blood flows through the first pump chamber 12a, the blood chamber 3 and the connection line 18 into the second pump chamber 13a. When both pump chambers 12a, 13a are filled with the desired volume, all the closure members are re-closed. This is followed by a second phase. At the start of the second phase, the control unit 30 switches the first and second pumps 12, 13 to the delivery operation and opens the second, fifth and seventh closure members 15, 19, 21. The blood from the pump chambers 12a, 13a is now returned via the return line 6 through the needle 9. The second phase is then followed again by the first phase. During the first and second phases, blood flows continuously through the dialyzer fluid chamber 3 of the dialyzer 1. It is not compulsory for all the closure members to be closed between the two phases. For example, the second and fifth closure members 15 and 19 may remain open.

FIG. 3 shows an alternative exemplary embodiment of the blood treatment device for single-needle dialysis. In this exemplary embodiment, the needle 9 is attached directly to the connector 5b of the feed line 5. Therefore, the section of the return line 6 attached to the Y-connection piece 7 is not necessary per se. The Y-connection piece may be omitted, which makes the structure even simpler. In other regards, the structure of the exemplary embodiment according to FIG. 2 is identical to the structure of the embodiment according to FIG. 1a. The pumps and closure members are driven as set forth below in the exemplary embodiment according to FIG. 2.

In the first phase, the control unit 30 (FIG. 1b) switches the first and second pumps 12, 13 to the intake operation and opens the first, second, fifth and sixth closure members 14, 15, 19, 20 and closes the third, fourth and seventh closure members 16, 17, 21, so that the two pump chambers 12a, 13a can fill with blood. In this case, blood flows through the first chamber 12a, the dialyzer fluid chamber 3, the connection line 18 into the second chamber 13a. In the subsequent second phase, the control unit 30 switches the chambers 12a, 13a to the delivery operation and opens the second, third, fifth and sixth closure members 15, 16, 19, 20 and closes the first, fourth and seventh closure members 14, 17, 21, so that the blood is returned from both chambers 12a, 13a via the feed line 5. In this case, blood flows through the dialyzer fluid chamber 3. All the closure members are re-closed between the two phases. This is not, however compulsory. For instance, the sixth closure member 20 may also remain open.

Figure 4:
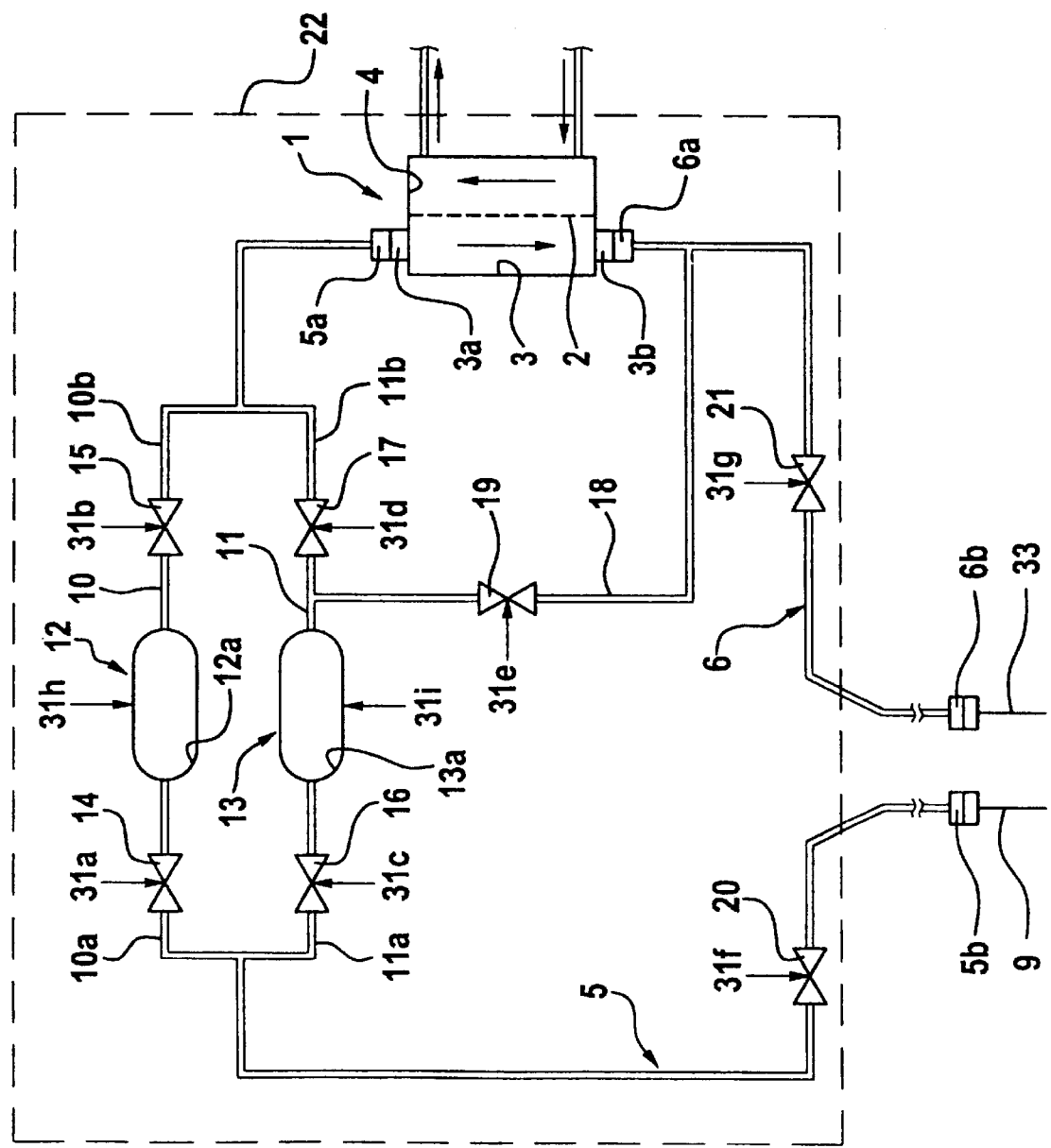
FIG. 4 shows a blood treatment device for dual-needle operation.

FIG. 4 shows the blood treatment device for dual-needle dialysis. The structure corresponds to the embodiments according to FIGS. 1 and 3. For dual-needle operation, an arterial needle is attached to the connector 5b of the feed line 5 and a venous needle 33 is attached to the connector 6b of the return line 6.

The sixth and seventh closure members 20, 21 are always open, and the fifth closure member 19 is always closed. During the first phase, the control unit 30 switches the first pump 12 to the intake operation and the second pump 13 to the delivery operation. The first and fourth closure members 14, 17 are opened and the second and third closure members 15, 16 are closed. While the first pump 12 is taking blood in through the arterial needle 9 via the feed line 5, the second pump 13 supplies the blood chamber 3 with blood that is returned via the return line 6 through the venous needle 33. After the first pump chamber 12a has been filled and the second pump chamber 13a has been emptied, the control unit 30 switches, in the second phase, the first pump 12 to the delivery operation and the second pump 13 to the intake operation and opens the second and third closure members 15, 16 and closes the first and fourth closure members 14, 17. The first pump 12 now supplies the blood chamber 3 with blood that is returned through the venous needle 33, while the second pump 13 takes blood in through the arterial needle 9.

Should complications arise with a patient's vascular accesses during dual-needle dialysis, the blood treatment device according to the invention may be refitted for single-needle dialysis with a few actions. To that end, changes to the needles 9, 33 and their contacts may possibly be necessary. Further, only the valve and pump control needs to be changed as described above, without there being a need to replace the disposable kit placed in the holding unit 22. In this way, very rapid refitting is possible.

While the foregoing description and drawings represent the preferred embodiments of the present invention, it will be apparent to whose skilled in the art that various changes and modifications may be made therein without departing from the true spirit and scope of the present invention.

What is claimed is:

1. A blood treatment device comprising:

a blood treatment unit having an inlet and an outlet;

a blood feed line connected to the inlet of the blood treatment unit, the blood feed line having a first branch line and a second branch line, wherein the first branch line and the second branch line are connected in parallel;

a blood return line connected to the outlet of the blood treatment unit;

a first positive displacement pump connected in the first line branch, the first pump divides the first line branch into a first section and a second section, a first closure member provided in the first section of the first line branch, a second closure member provided in the second section of the first line branch;

a second positive displacement pump connected in the second line branch, the second pump divides the second line branch into a first section and a second section, a third closure member provided in the first section of the second line branch, a fourth closure member provided in the second section of the second line branch; and a connection line that branches off from the blood return line and connects the outlet of the blood treatment unit to one of the first line branch and the second line branch, a fifth closure member provided in the connection line.

2. The blood treatment device as claimed in claim 1, wherein the connection line connects the blood return line to the second section of the second line branch.

3. The blood treatment device as claimed in claim 1, further comprising:

a common blood line connecting the blood feed line and the blood return line;

a needle attached to the common blood line;

an additional closure member provided in the blood return line;

a control unit provided for opening and closing the closure members and for activating the first pump and the second pump, the control unit connected to the closure members, the first pump and the second pump, and designed so that during a first phase, the first pump and the second pump are configured to conduct an intake operation, the first closure member is open, the second closure member is open, the fifth closure member is open, the third closure member is closed, the fourth closure member is closed, and the additional closure member is closed, and during a second phase, the first pump and the second pump are configured to conduct a delivery operation, the second closure member is open, the fifth closure member is open, the additional closure member is open, the first closure member is closed, the third closure member is closed, and the fourth closure member is closed.

4. The blood treatment device as claimed in claim 3, wherein the first closure member is closed, the second closure member is closed, the third closure member is closed, the fourth closure member is closed, and the fifth closure member is closed, when the first pump and the second pump are changed from the intake operation to the delivery operation.

5. The blood treatment device as claimed in claim 1, further comprising:
   a needle attached to the blood feed line,
   a control unit provided for opening and closing the closure members and for activating the pumps, the control unit connected to the closure members, the first pump and the second pump, and designed so that
      during a first phase, the first pump and the second pump are configured to conduct an intake operation, the first closure member is open, the second closure member is open, and the fifth closure member is open, the third closure member is closed, and the fourth closure member is closed, and
      during a second phase, the first pump and the second pump are configured to conduct a delivery operation, the second closure member is open, the third closure member is open, the fifth closure member is open, the first closure member is closed, and the fourth closure member is closed.

6. The blood treatment device as claimed in claim 5, wherein the first closure member is closed, the second closure member is closed, the third closure member is closed, the fourth closure member is closed, and the fifth closure member is closed, when the first pump and the second pump are changed from the intake operation to the delivery operation.

7. The blood treatment device as claimed in claim 1, further comprising
   an arterial needle attached to the blood feed line;
   a venous needle attached to the blood return line;
   a control unit provided for opening and closing the closure members and activating the pumps, the control unit connected to the closure members, the first pump and the second pump, and designed so that
      during a first phase, the first pump is configured to conduct an intake operation and the second pump is configured to conduct a delivery operation, the first closure member is open, the fourth closure member is open, the second closure member is closed, the third closure member is closed, and the fifth closure member is closed, and
      during a second phase, the first pump is configured to conduct a delivery operation and the second pump is configured to conduct an intake operation, the second closure member is open, the third closure member is open, the first closure member is closed, the fourth closure member is closed, and the fifth closure members is closed.

8. The blood treatment device as claimed in claim 7, wherein the first closure member is closed, the second closure member is closed, the third closure member is closed, the fourth closure member is closed, and the fifth closure member is closed, when the first pump is changed from intake operation to delivery operation and the second pump is changed from delivery operation to intake operation.

9. The blood treatment device as claimed in claim 1, wherein the closure members are electromagnetic actuable clamp devices.

10. The blood treatment device as claimed in claim 1, wherein the closure members are pneumatically actuable clamp devices.

11. The blood treatment device as claimed in claim 1, wherein the first pump is a diaphragm pump and the second pump is a diaphragm pump.

12. The blood treatment device as claimed in claim 1, wherein the first pump and the second pump each respectively has a pump chamber that is designed as a replaceable unit, the pump chamber of the first pump connected into the first line branch of the blood feed line and the pump chamber of the second pump connected into the second line branch of the blood feed line.

13. The blood treatment device as claimed in claim 12, wherein the blood feed line, the blood return line, the connection line, and the pump chambers of the first and second pumps are designed as a disposable kit.

14. A disposable kit for a blood treatment device, comprising:
   a blood feed line that has two parallel line branches;
   a blood return line;
   a first pump chamber connected into the first line branch;
   a second pump chamber connected into the second line branch; and
   a connection line that connects the blood return line to one of the first line branch and the second line branch.

15. The disposable kit as claimed in claim 14, further comprising:
   a first connector provided at a free end of the blood feed line for attachment of a needle, and
   a second connector provided at a free end of the blood return line for attachment of a needle.

16. The disposable kit as claimed in claim 14, further comprising:
   a Y-connection piece configured for connection to a free end of the blood return line and a free end of the blood feed line, the Y-connection piece for attachment of a needle.

* * * * *